United States Patent
McCroskey et al.

(10) Patent No.: US 7,195,923 B2
(45) Date of Patent: Mar. 27, 2007

(54) RATIOMETRIC DETERMINATION OF GLYCATED PROTEIN

(75) Inventors: Ralph P. McCroskey, San Diego, CA (US); Cameron E. Melton, Nine Mile Falls, WA (US)

(73) Assignee: Scripps Laboratories, Inc., San Diego, CA (US)

( * ) Notice: Subject to any disclaimer, the term of this patent is extended or adjusted under 35 U.S.C. 154(b) by 291 days.

(21) Appl. No.: 10/061,438

(22) Filed: Jan. 31, 2002

(65) Prior Publication Data

US 2003/0068830 A1    Apr. 10, 2003

Related U.S. Application Data

(60) Provisional application No. 60/265,229, filed on Jan. 31, 2001.

(51) Int. Cl.
*G01N 33/00* (2006.01)
*G01N 33/573* (2006.01)

(52) U.S. Cl. .......................... 436/87; 435/7.4; 435/7.6; 435/7.7; 435/7.8; 435/7.9; 435/7.92; 435/14; 435/179; 435/180; 435/181; 435/188; 435/287.7; 435/287.9; 435/288.3; 435/288.7; 435/803; 435/805; 435/815; 435/817; 435/962; 435/967; 435/970; 435/973; 436/501; 436/14; 436/15; 436/16; 436/18; 436/46; 436/129; 436/131; 436/151; 436/66; 436/67; 436/88; 436/161; 436/162; 436/164; 436/166; 436/169; 436/174; 436/175; 436/177; 436/178; 436/805; 436/810; 436/815; 436/825; 422/56; 422/57; 422/70; 530/369; 530/385; 530/395; 530/403; 530/413; 530/415; 530/416; 530/417; 210/660; 210/663; 210/668; 210/500.29; 210/500.34; 210/500.35; 210/500.38; 210/500.42; 600/477; 356/39; 356/40

(58) Field of Classification Search ................. 435/7.4, 435/7.6, 7.9, 7.92, 7.7, 7.8, 14, 179, 180, 435/181, 188, 287.7, 287.9, 288.3, 288.7, 435/803, 805, 815, 817, 962, 967, 970, 973; 436/501, 67, 161–162, 164, 14, 15, 16, 18, 436/46, 129, 131, 151, 66, 87, 88, 166, 169, 436/174, 175, 177, 178, 805, 810, 815, 825; 530/413, 369, 385, 395, 403, 415, 416, 417; 422/70, 56, 57; 210/663, 668, 660, 500.29, 210/500.34, 500.35, 500.38, 500.42; 600/477; 356/39, 40, 433; 521/32, 901; 523/344; 524/195, 183, 404, 405, 701; 527/301, 311; 528/69; 560/334; 427/308, 324, 339, 415, 427/439

See application file for complete search history.

(56) References Cited

U.S. PATENT DOCUMENTS

| | | | | |
|---|---|---|---|---|
| 3,226,380 A | * | 12/1965 | Knight | 536/56 |
| 4,130,470 A | * | 12/1978 | Rosengren et al. | 204/451 |
| 4,269,605 A | | 5/1981 | Dean et al. | 23/230 B |
| 4,298,500 A | * | 11/1981 | Abbott | 502/7 |
| 4,371,374 A | * | 2/1983 | Cerami et al. | 436/87 |
| 4,407,961 A | * | 10/1983 | Sanders | 436/67 |
| 4,409,335 A | * | 10/1983 | Hanamoto et al. | 436/67 |
| 4,477,575 A | | 10/1984 | Vogel et al. | 436/170 |
| 4,678,757 A | | 7/1987 | Rapkin et al. | 436/169 |
| 4,820,636 A | * | 4/1989 | Hill et al. | 435/14 |
| 4,861,728 A | | 8/1989 | Wagner | 436/501 |
| 4,917,685 A | * | 4/1990 | Viswanathan et al. | 604/891.1 |
| 4,925,545 A | * | 5/1990 | Murel | 204/459 |
| 5,064,866 A | * | 11/1991 | Toyomoto et al. | 521/27 |
| 5,110,745 A | | 5/1992 | Kricka et al. | 436/87 |
| 5,179,005 A | * | 1/1993 | Phillips et al. | 435/14 |
| 5,242,842 A | * | 9/1993 | Sundrehagen | 436/536 |
| 5,284,777 A | | 2/1994 | Rosenthal et al. | 436/518 |
| 5,298,410 A | * | 3/1994 | Phillips et al. | 435/188 |
| 5,384,239 A | * | 1/1995 | Saunders | 435/2 |

(Continued)

U.S. PATENT DOCUMENTS

| | | | |
|---|---|---|---|
| 5,389,381 A * | 2/1995 | Phillips et al. | 424/94.3 |
| 5,439,591 A * | 8/1995 | Pliura et al. | 210/635 |
| 5,506,144 A | 4/1996 | Sundrehagen | 436/66 |
| 5,529,915 A * | 6/1996 | Phillips et al. | 435/188 |
| 5,532,150 A * | 7/1996 | Snow et al. | 435/188 |
| 5,536,382 A * | 7/1996 | Sunzeri | 204/451 |
| 5,585,216 A * | 12/1996 | Baur et al. | 430/108.1 |
| 5,589,393 A * | 12/1996 | Fiechtner et al. | 436/15 |
| 5,661,020 A * | 8/1997 | Snow et al. | 435/188 |
| 5,695,949 A * | 12/1997 | Galen et al. | 435/14 |
| 5,718,895 A * | 2/1998 | Asgharian et al. | 424/94.1 |
| 5,719,053 A * | 2/1998 | Noffsinger et al. | 435/288.6 |
| 5,725,774 A | 3/1998 | Neyer | 210/645 |
| 5,739,318 A * | 4/1998 | Frantzen et al. | 540/128 |
| 5,763,203 A * | 6/1998 | Ugelstad et al. | 435/7.24 |
| 5,763,238 A * | 6/1998 | James et al. | 436/172 |
| 5,773,645 A * | 6/1998 | Hochstrasser | 204/456 |
| 5,800,602 A * | 9/1998 | Baur et al. | 106/162.2 |
| 5,801,053 A * | 9/1998 | Noffsinger et al. | 435/288.6 |
| 5,807,747 A * | 9/1998 | Wallworth et al. | 436/67 |
| 5,843,788 A * | 12/1998 | Rexroad et al. | 436/161 |
| 5,846,741 A * | 12/1998 | Griffiths et al. | 435/7.5 |
| 5,877,025 A * | 3/1999 | Edwards et al. | 436/67 |
| 5,919,708 A * | 7/1999 | Sundrehagen | 436/66 |
| 5,959,076 A * | 9/1999 | Nagel et al. | 530/322 |
| 5,963,335 A * | 10/1999 | Boutelle | 356/433 |
| 5,985,121 A * | 11/1999 | Wu et al. | 204/601 |
| 6,020,203 A * | 2/2000 | Rexroad et al. | 436/67 |
| 6,054,039 A * | 4/2000 | Shieh | 205/778 |
| 6,083,653 A * | 7/2000 | Baur et al. | 430/108.3 |
| 6,121,050 A * | 9/2000 | Han | 436/95 |
| 6,174,734 B1 * | 1/2001 | Ito et al. | 436/518 |
| 6,304,766 B1 * | 10/2001 | Colvin, Jr. | 600/317 |
| 6,323,322 B1 * | 11/2001 | Filpula et al. | 530/387.3 |
| 6,330,464 B1 * | 12/2001 | Colvin et al. | 600/316 |
| 6,387,672 B1 * | 5/2002 | Arimori et al. | 435/183 |
| 6,399,293 B1 * | 6/2002 | Pachl et al. | 435/4 |
| 6,562,581 B2 * | 5/2003 | Law et al. | 435/14 |
| 6,627,177 B2 * | 9/2003 | Singaram et al. | 424/9.6 |
| 6,653,141 B2 * | 11/2003 | Singaram et al. | 436/95 |
| 6,673,625 B2 * | 1/2004 | Satcher et al. | 436/94 |
| 6,677,158 B2 | 1/2004 | Hud et al. | 436/67 |
| 6,682,938 B1 * | 1/2004 | Satcher et al. | 436/172 |
| 6,711,423 B2 * | 3/2004 | Colvin, Jr. | 600/317 |
| 6,740,257 B2 * | 5/2004 | Arimori et al. | 252/301.16 |
| 6,743,896 B2 * | 6/2004 | Filpula et al. | 530/387.3 |
| 6,743,908 B2 * | 6/2004 | Filpula et al. | 536/23.53 |
| 6,766,183 B2 * | 7/2004 | Walsh et al. | 600/317 |
| 6,818,416 B2 * | 11/2004 | Pachl et al. | 435/25 |
| 6,927,246 B2 * | 8/2005 | Noronha et al. | 524/184 |
| 6,984,526 B2 * | 1/2006 | Garcia-Rubio et al. | 436/171 |
| 7,018,843 B2 * | 3/2006 | Heller | 436/95 |
| 7,045,361 B2 * | 5/2006 | Heiss et al. | 436/172 |
| 7,078,480 B2 * | 7/2006 | Nagel et al. | 530/322 |

FOREIGN PATENT DOCUMENTS

| | | | |
|---|---|---|---|
| DE | 3720736 A1 | | 1/1989 |
| EP | 0 455 225 B1 | | 3/1995 |
| GB | 2 024 829 | | 1/1980 |
| GB | 2206411 | * | 1/1989 |
| JP | 60-58936 | | 3/1994 |
| WO | WO 96/03657 | | 2/1996 |
| WO | WO 98/40750 | | 9/1998 |

OTHER PUBLICATIONS

Yan, J. et al. The relationship among pKa, pH, and binding constants in the interactions between boronic acids and diols—it is not as simple as it appears. TETRAHEDRON. 2004;60:11205-11209.*
Tang, Z. et al. Effects of pH on glucose measurements with handheld glucose meters and a portable glucose analyzer for point-of-care testing. Arch. Pathol. Lab. Med. 2000;124:577-582.*
Kikuchi, A. et al. Glucose-sensing electrode coated with polymer complex gel containing phenylboronic acid. Anal. Chem. 1996;68:823-828.*
Liu, X.C. & Scouten, W.H., Studies on oriented and reversible immobilization of glycoprotein using novel boronate affinity gel. J. Molec. Recognit. 1996;9:462-467.*
Ackloo, S.Z. et al. Structural analysis of diols by electrospray mass spectrometry on boric acid complexes. Rapid Commun. Mass Spectrom. 1999;13:2406-2415.*
Penn, S.G. et al. Direct analysis of sugar alcohol borate complexes in plant extracts by matrix-assisted laser desorption/ionization fourier transform mass spectrometry. Anal. Chem. 1997;69:2471-2477.*
Sartobind(R) product literature, Sartorius AG, Publication Nos. SL-1513-e05043, SL-2014-e03082, SL-2018-e06054, relevant websites and documents included in Application file history, available at <http://www.sartorius.com> (last updated Jul. 7, 2006).*
Freitag, R. et al. Controlled mixed-mode interaction chromatography on membrane adsorbers. J. Chromatogr. A. 1996;728:129-137.*
Szulc, M. et al. Detection in liquid chromatography. Methods Enzymol. 1996;270:175-200.*
Khym, J.X. The use of the borate complex. Methods Enzymol. 1967;12:93-101.*
Mao, Q. & Pawliszyn, J. Capillary isoelectric focusing with whole column imaging detection for analysis of proteins and peptides. J. Biochem. Biophys. Methods. 1999;39:93-110.*
Shapiro, R. et al. Sites of nonenzymatic glycosylation of human hemoglobin A. J. Biol. Chem. 1980;255:3120-3127.*
Wu, J. & Pawliszyn, J. Protein analysis by isoelectric focusing in a capillary array with an absorption imaging detector. J. Chromatogr. B. 1995;669:39-43.*
DiCesare, N. & Lakowicz, J.R. Fluorescent probe for monosaccharides based on a functionalized boron-dipyrromethene (BODIPY) with a boronic acid group. Tetrahedron Lett. 2001;42:9105-9108.*
American Diabetes Association, Tests of Glycernia in Diabetes, *Diabetes Care*, vol. 20, Supp. 1 (Jan. 1997) pp. S18-S20.
Diabetes Control and Complications Trial Research Group, The Effect of Intensive Treatment of Diabetes on the Development and Progression of Long-Term Complications in Insulin-Dependent Diabetes Mellitus, *New England Journal of Medicine*, 329(14):977-986 (1993).
Matrisian L.M., et al., Stromelysin/transin and tumor progression, *Cancer Biology*, vol. 1 (1990): pp. 107-115.

* cited by examiner

*Primary Examiner*—Long V. Le
*Assistant Examiner*—David J. Venci
(74) *Attorney, Agent, or Firm*—Knobbe, Martens, Olson & Bear LLP

(57) ABSTRACT

The present invention provides methods for determining a ratio of an amount of a glycated form of a protein to a total amount of the protein in a sample containing the glycated protein, the glycosylated protein, or the glycoprotein. The method incorporates lateral flow test strip or vertical flow test strip devices having negatively charged carboxyl or carboxylate groups and hydroxyboryl groups immobilized and interspersed on a solid support matrix. The solid support matrix may include derivatives of cellulose (e.g., carboxy cellulose) derivatized with carboxylic acid (e.g., carboxylate, carboxyl) groups and hydroxyboryl compounds including phenylboronic acid (e.g., phenylborate), aminophenylboronic acid, boric acid (e.g., borate), or other boronic acid (e.g., boronate) compounds. The present invention is usefi.il for monitoring glycation or glycosylation of hemoglobin or albumin for monitoring glycemic control (e.g., glycemia in diabetes).

27 Claims, 10 Drawing Sheets

Lateral Flow

Vertical Flow

Combination

RATIOMETRIC DETERMINATION OF GLYCATED PROTEIN

PRIORITY INFORMATION

This application claims priority to U.S. application Ser. No. 60/265,229, filed Jan. 31, 2001.

FIELD OF THE INVENTION

This invention relates to a method for the quantitation of percent glycated protein in a biological sample suitable for use with a reflectance meter such as used in the self monitoring of blood glucose concentration by diabetics.

BACKGROUND OF THE INVENTION

Control of blood glucose concentrations in diabetics has been shown to decrease the frequency and severity of long-term microvascular and neurologic complications of the disease. The measurement of glycated hemoglobin and protein in blood are used to determine how well blood glucose concentration has been managed over an extended time period.

The rate of formation of glycated hemoglobin is directly related to the glucose concentration in blood.

The average red blood cell life span is 120 days, so quantitation of the percent glycation of hemoglobin has been correlated to a measure of the average glucose concentration over the previous 2 to 3 months which is a measure of glycemic control over that time period (see "Diabetes Control and Complications Trial Research Group, The effect of intensive treatment of diabetes on the development of progression of long-term complications in insulin-dependent diabetes mellitus", New England Journal of Medicine, 329, 977–986 (1993), and "American Diabetes Association, Tests of Glycemia in Diabetes", Diabetes Care, 20 (suppl. 1), S18–S20 (1997)).

Glucose also attaches to non-hemoglobin proteins in blood, for example albumin. Since albumin is the most abundant serum protein and its circulating half-life is about 20 days, the concentration of glycated protein is a measure of the average glucose concentration over the previous 2 to 3 weeks. The measure of glucose directly gives the glucose concentration at the time of measurement.

An immobilized dihydroxyboryl compound has been reported as useful to bind to the 1,2 cis diols of the carbohydrate of glycated proteins to separate them from non-glycated proteins. Use of this technology in a column chromatography method to determine percent glycation has been reported (see, U.S. Pat. No. 4,269,605 issued May 26, 1981 to Dean and U.S. Pat. No. 5,284,777, issued Feb. 8, 1994 to Rosenthal). These methods are said to use the boronate derivative immobilized onto agarose beads in a column to separate glycated from non-glycated proteins in the sample. These methods require specific dilutions and pipettings of the sample so as to not overload the capacity of the affinity binder affixed to the agarose beads. The use of a boronate derivative immobilized on agarose beads would not appear to lend itself to a strip application.

U.S. Pat. No. 5,110,745 issued May 5, 1992 to Kricka, et al., is said to describe methods of detecting glycated protein in a sample wherein the sample is contacted with a defined excess of a boronate compound in solution. The resulting unbound boronate is said to be measured by binding it to an immobilized glycated molecule on a support matrix and measuring the amount of glycated molecule left un-complexed. This method appears to require a number of steps including, a separate reaction in solution before application to a solid support, dilution of the sample to assure that the amount of binder added to the biological sample is in excess, performance of a separate assay to determine the percentage of protein glycation and multiple binding and washing steps.

A dipstick method for the measurement of glycated hemoglobin is said to be described in U.S. Pat. No. 4,861,728 issued Aug. 29, 1989 to Wagner. This method is said to involve contacting of a hemoglobin binding agent linked to a solid support with a lysed blood sample previously mixed with a dihydroxyboryl compound linked to a fluorescent label. The support is said to bind non-glycated hemoglobin and fluorescent labeled glycated hemoglobin. The fluorescent label is said to bind to glycated hemoglobin through the dihydroxyboronyl compound. The solid phase is removed from the sample and total hemoglobin is measured by reflectance photometry while glycated hemoglobin is measured using fluorescence. This method is said to require an addition of an amount of fluorescent labeled dihydroxyboryl reagent to the sample and a rinsing step after it is removed from the sample. Further it requires two different measurement methods for the quantitation.

In other assays, (see, e.g., Japanese Pat. No. 6,058,936, European Pat. No. 455225, and published PCT application WO 96/03657) a boronate derivative coupled to a detectable label (such as a fluorescent compound, a chemiluminescent compound, isotope, enzyme or other label) is said to be used. Both the glycated and non-glycated proteins are bound to a solid support using a general affinity binder such as an antibody. The boronate-label complex is added and the amount of label that remains bound to the solid support is measured. Each of these types of methods requires the additional step of labeling the glycated protein. In addition, these assays use different measurement methods to quantitate total and glycated proteins.

Published PCT application WO 9840750 (published Sep. 17, 1998) is said to describe a method of determining the percentage of glycated hemoglobin in which immobilized boronate binds glycated hemoglobin in the sample. The amount of glycated hemoglobin bound is said to be proportional to the fraction of glycated hemoglobin in the sample. This is said to eliminate the need for measuring nonglycated hemoglobin to determine the percent glycation. However, it appears the method results may vary depending on the incubation time of glycated protein with the boronated support.

Consequently, there is a need for a simple, fast and efficient method to quantitate the amount of glycated protein in a biological sample that does not require dilution of the sample, requires minimal procedural steps, may be utilized in conjunction with a simple detection device such as a hand held reflectance meter, and is adaptable to a standard strip assay.

SUMMARY OF THE INVENTION

The present invention is directed to methods for the quantitation of glycated proteins in a biological sample, devices utilizing these methods and kits comprising these devices.

The results from measurement of glucose, glycated protein and glycated hemoglobin may provide a more complete picture of glycemic control. Measurement of immediate glucose concentration may be used for adjustment of medications, diet or exercise. For measurement of medium term glycemic control, measurement of glycated albumin concentration may allow one to follow effects of recent changes in lifestyle. For measurement of long term glycemic control, measurement of glycated hemoglobin concentration may allow one to monitor overall effects of changes. It would be convenient to have a test for all three in a format that could be used in a doctor's office lab so results could be discussed with the patient during the visit or, alternatively, used by the patient at home. Currently, blood glucose is routinely monitored using hand held meters and easy to use strips. Unfortunately, similar tests for glycated proteins and hemoglobin have not been available.

The methods of the present invention provide methods of quantitating glycated protein in a biological sample. The biological sample is contacted with a solid support matrix under conditions where both glycated and non-glycated protein are bound to the solid support matrix. An amount of a first buffer is added sufficient to rinse off unbound protein. A first bound protein measurement is made to determine total (glycated and non-glycated) bound protein. A second buffer is added to the solid support matrix which changes the conditions so that glycated protein is bound and non-glycated protein is not substantially bound and is added in an amount sufficient to rinse off unbound (non-glycated) protein. A second bound protein measurement is made. Glycated protein is quantitated using the first and second bound protein measurements.

According to one aspect, the present invention is directed to a method of quantitation of glycated protein in a sample which comprises: (a) contacting a solid support matrix which comprises a negatively charged group and a hydroxyboryl compound and which has a measurement area, with an aliquot of biological sample sufficient to cover said measurement area; (b) contacting said solid support matrix with an aliquot of a first buffer sufficient to rinse off unbound protein, wherein said first buffer has a pH selected to allow both glycated and non-glycated protein to be bound to said solid support matrix;(c) quantitating protein bound to said measurement area using measurement of a selected property of said protein to give a first bound protein reading; (d) contacting said solid support matrix with an aliquot of a second buffer sufficient to rinse off unbound protein, wherein said second buffer has a pH selected to allow glycated protein to be bound to said solid support matrix but where non-glycated protein is not substantially bound to said solid support matrix; (e) quantitating protein bound to said measurement area using measurement of the property measured in step (c) to give a second bound protein reading; and (f) calculating percentage of glycated protein using said first and second bound protein readings.

According to an alternate aspect, the present invention is directed to a method for quantitation of amount of glycated protein in a biological sample which compromises: (a) contacting a solid support matrix which comprises a negatively charged group and a hydroxyboryl compound and which has a measurement area with an aliquot of a biological sample sufficient to cover said measurement area; (b) contacting said solid support matrix with an aliquot of a first buffer sufficient to rinse off unbound protein, wherein said first buffer has a pH of about 5.0 to about 7.0; (c) quantitating protein bound to said measurement area to give a first bound protein reading; (d) contacting said solid support matrix with an aliquot of second buffer sufficient to rinse off unbound protein, wherein said buffer has a pH of about 8.0 to about 10.0; (e) quantitating protein bound to said measurement area to give a second bound protein reading; and (f) calculating percentage of glycated protein in said sample using said first bound protein reading and said second bound protein reading.

Preferably, and for convenience, the first and second bound protein readings measure the same property. Preferably, the property measured is an optical reading. More preferably, the optical reading is absorbance or reflectance at a specified wavelength.

According to one preferred aspect of the present invention, a method for quantitation of glycated hemoglobin in a biological sample is provided which comprises: (a) bringing the biological sample into contact with a solid support matrix which comprises negatively charged groups and a dihydroxyboryl compound and which has a measurement area, at a sample application site which is in communication with the solid support matrix; (b) adding an aliquot of a first buffer at the sample application site wherein the first buffer has a pH of about 5.0 to about 7.0; (c) making a first optical reading of said measurement area at a wavelength at which hemoglobin absorbs light; (d) adding an aliquot of a second buffer at the sample application site wherein the second buffer has a pH of about 8.0 to about 10.0; (e) making a second optical reading of the measurement area at a wavelength at which hemoglobin absorbs light; and (f) calculating the percentage of glycated hemoglobin in the blood sample using the first and second optical readings. Where the biological sample is a blood sample comprising red blood cells, the sample is contacted with a red blood cell lysing agent before the first optical reading is made. The blood sample may be pre-treated with a red blood cell lysing agent prior to being brought into contact of the solid support. Alternatively, the first buffer may further comprise a red blood cell lysing agent or the solid support matrix may be treated with a red blood cell lysing agent before it comes in contact with the biological sample.

According to another preferred aspect of the present invention, a method for quantitation of a glycated non-hemoglobin protein is provided which comprises: (a) bringing the biological sample into contact with a sample application site which is in communication with a solid support matrix which comprises negatively charged groups and a dihydroxyboryl compound and which has a measurement area; (b) adding an aliquot of a first buffer to the sample application site wherein the first buffer has a pH between about 5.0 and about 7.0; (c) making a first optical reading of the measurement area at a wavelength at which the protein absorbs light; (d) adding an aliquot of a second buffer to the sample application site wherein the second buffer has a pH between about 8.0 and about 10.0; (e) making a second optical reading of the sample application site at a wavelength at which the protein absorbs light; and (f) calculating the percentage of glycated protein in the biological sample using the first and second optical readings. Suitable biological samples for use in the method of this aspect of the present invention include plasma and serum samples. A suitable glycated protein for quantitation according to this aspect is albumin. For the quantitation of certain glycated proteins it may be preferred that the protein be labeled with a suitable protein specific labeling agent.

Preferred buffer systems for use as the first buffer include MES [2(N-morpholino) ethanesulfonic acid], MOPS [3(N-morpholino)propanesulfonic acid] and HEPES [N-2-hydroxyethylpiperazine-N'-2-ethanesulfonic acid].

Preferred buffers for use as the second buffer include ammonium acetate and taurine buffers.

According to another aspect of the present invention, a diagnostic device for quantitation of glycated protein utilizing the methods above is provided. Preferably the protein is hemoglobin or albumin.

In another aspect, a kit is provided which comprises the diagnostic device described above; a first buffer having a pH of about 5.0 to about 7.0; and a second buffer having a pH of about 8.0 to about 10.0.

Definitions

In accordance with the present invention and as used herein, the following terms are defined to have the following meanings, unless explicitly stated otherwise:

The term "alkyl" refers to saturated aliphatic groups including straight-chain, branched-chain and cyclic (including polycyclic) groups.

The term "carboxylate" or "carboxy" refers to the group —COOH.

The term "phosphate" refers to the group —$PO_4$.
The term "sulfate" refers to the group —$SO_4$.
The term "sulfinate" refers to the group —$SO_2H$.
The term "sulfonyl" refers to the group —$SO_3H$.
"Hb" refers to hemoglobin.
"HEPES" refers to [N-2-hydroxyethylpiperazine-N'-2-ethanesulfonic acid].
"K", when used in the context of measurement of amount of light absorbed and reflectance, refers to the absorption coefficient.
"MES" refers to [2(N-morpholino)ethanesulfonic acid].
"MOPS" refers to [3-(N-morpholino)propanesulfonic acid].
"S", when used in the context of measurement of amount of light absorbed and reflected, refers to the scattering coefficient.

BRIEF DESCRIPTION OF THE DRAWINGS

FIG. 16A depicts a plot of results obtained using an assay of the present invention (See Example 9) versus results obtained using the Roche® Integra 400 (Roche Diagnostics). FIG. 16B depicts a plot of results obtained using an assay of the present invention (See Example 9) versus results obtained using the DCA 2000 (Bayer).

DETAILED DESCRIPTION OF THE INVENTION

Figure 1:
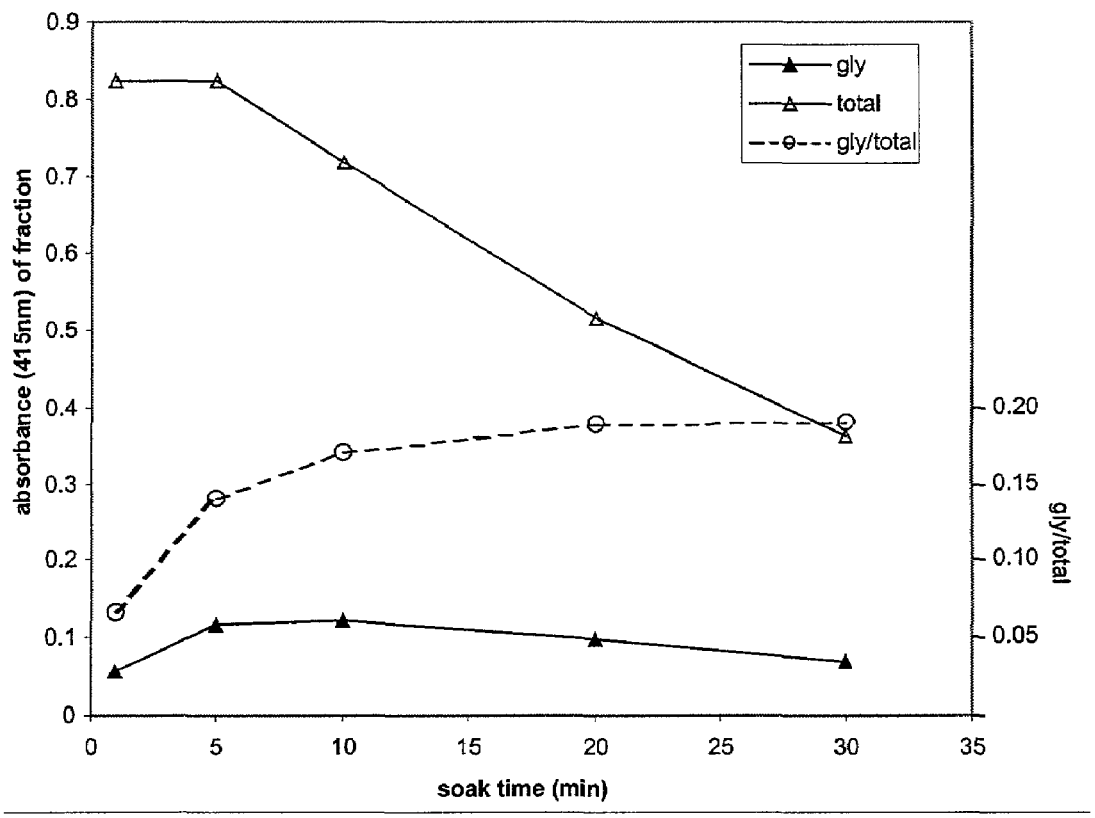
FIG. 1 depicts a graph of the absorbance of glycated hemoglobin (closed triangles) and total hemoglobin (open triangles) bound to the solid support in the assay and a graph of the ratio of glycated to total hemoglobin (open circles) versus soak time. Different supports were used, having been derivatized with boronate for increasing lengths of time.

According to one aspect, the present invention provides a method for quantitation of glycated proteins in a biological sample in which the sample and reagent(s) are applied to a solid support matrix which preferably comprises a negatively charged group and a dihydroxyboryl compound. Measurement of the total and glycated proteins is done at a single location on the solid support. This measurement may conveniently be done by measuring a selected property of the protein. Advantageously, this method does not require measurement of the volume of biological sample.

In one aspect, the present invention is directed to a method for quantitation of glycated protein in a sample in which a solid support matrix which comprises a negatively charged group and a hydroxyboryl compound and which has a measurement area is contacted with an aliquot of the biological sample sufficient to cover the measurement area. The solid support matrix is then contacted with a first buffer which has a pH selected so as to allow both glycated and non-glycated protein to be bound to the solid state matrix, in an amount sufficient to rinse off unbound protein. The amount of protein bound to the measurement area is quantitated by measurement of a selected property of the protein to give a first bound protein reading. The solid support matrix is then contacted with a second buffer which has a pH selected to allow glycated protein to be bound to the solid support matrix but where non-glycated protein is not substantially bound to the solid support matrix, in an amount sufficient to rinse off unbound protein. The amount of protein bound to the measurement area is quantitated by measurement of the same selected property (as used to obtain the first bound protein reading) to give a second bound protein reading. The percentage of glycated protein is calculated using the first and second bound protein readings.

According to an alternate aspect, the present invention is directed to methods of quantitation of glycated protein in a sample in which a solid support matrix which comprises a negatively charged group and a hydroxyboryl compound and which has a measurement area is contacted with an aliquot of a biological sample sufficient to cover the measurement area. The solid support matrix is then contacted with a first buffer which has a pH of about 5.0 to about 7.0 in an amount sufficient to rinse off unbound protein. The amount of protein bound to the measurement area is quantitated to give a first bound protein reading. The solid support matrix is then contacted with a second buffer which has a pH of about 8.0 to about 10.0 in an amount sufficient to rinse off unbound protein. The amount of protein bound to the measurement area is quantitated to give a second bound protein reading. The percentage of glycated protein in the biological sample is calculated using the first bound protein reading and the second bound protein reading.

The methods of the present invention may conveniently be used to quantitate amounts of either glycated hemoglobin or glycated non-hemoglobin protein (such as albumin).

In the quantitation of glycated hemoglobin, typically a blood sample is used. The blood sample is contacted with a red blood cell lysing agent before the first bound protein reading is made. The sample may be contacted with the red blood cell lysing agent prior to being added to the solid support (such as by pretreatment of the sample). Also, the red blood cell lysing agent may be added to the solid support by a pre-rinse before sample is added to the support. Alternatively, the first buffer may include a red blood cell lysing agent. Suitable red blood cell lysing agents are known to those of skill in the art and include Triton X-100 and Igepal CA-630.

Preferably, the first and second bound protein readings involve an optical reading. More preferably, the selected property measured is absorbance or reflectance at a specified wavelength.

According to a preferred aspect of the present invention, the dihydroxyboryl compound of said solid support matrix has the structure;

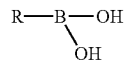

wherein R is selected from the group consisting of phenyl, substituted phenyl, hydrogen, and alkyl of 1 to about 6 carbon atoms. When R is alkyl, suitable alkyl groups include ethyl, 1-propyl, and 3-methyl-1-butyl. Preferably R is m-amino-phenyl.

Suitable solid support matrices include supports selected from the group consisting of cellulose, nitrocellulose, cellulose acetate, polyacrylamide, agarose polyacrylaminde copolymer, agarose, starch, nylon, nylon polyesters, dextran, cross-linked dextran, dextran acrylamide copolymer, cross-linked hydroxyethylmethacrylate substituted cross-linked polystyrenes, polyvinylalcohol, wool, metal oxides, porous ceramics coated with hydrophilic organic polymers and glass. Preferably the solid support matrix comprises a negatively charged group. A preferred solid support matrix is cellulose. Preferably the negatively charged group is selected from the group consisting of phosphate, sulfate, sulfonate, sulfinate and carboxylate (or carboxy). Preferably the negatively charged group is carboxylate.

I The Assay

According to one aspect of the method of the present invention both glycated and non-glycated protein are bound to a solid support matrix comprising a negatively charged group and an immobilized dihydroxyboryl containing compound under one pH condition. The bound non-glycated protein is then selectively removed under a second pH condition. The glycated protein remains bound to the support under the second pH condition. The measurement of total protein is made following the binding under the first pH condition. The measurement of glycated protein is made after rinsing the support-bound protein complex under the second pH condition to remove unbound protein. The percent glycation is calculated from the percent of the second measurement relative to the first. This assay is particularly useful for the measurement of glycated hemoglobin and glycated protein in a blood, serum or plasma sample.

The method may be used for a biological sample such as capillary blood, whole blood, serum or plasma. According to a preferred aspect, one wavelength may be used for both measurements (total and glycated). The assay is easily adaptable to be used with the same meters that are used in self blood glucose monitoring by diabetics. Since both measurements may be made at the same location on the solid support (see Example 5), any differences in the support from location to location would not interfere with the results.

II Solid Support Matrix and Immobilized Binder

The solid support matrix may be one of a number of natural or synthetic polymeric materials to which can be bound negatively charged groups and the dihydroxyboryl compound and through which the sample and reagents can pass. Suitable support matrices include, for example, cellulose, nylon, nitrocellulose cellulose acetate, polyacrylamide, agarose polyacrylamide copolymer agarose, starch, nylon polyesters, dextran, cross-linked dextran, dextran acrylamide copolymer, cross-linked hydroxyethylmethacrylate substituted cross-linked polystyrenes and polyvinyl alcohol. Other supports that may be utilized with the present invention include those listed in U.S. Pat. No. 4,269,605. In addition, other suitable supports are known to those of skill in the art. A preferred solid support matrix is cellulose paper.

The dihydroxyboryl compound (preferably phenylboronic, boric or other boronic acids, more preferably m-aminophenyboronic acid) may be bound to the solid support by mechanical, physical or chemical means, preferably by a covalent chemical bond. Binding to the solid support matrix can be by methods known in the art. Such methods include, for example, those listed in U.S. Pat. No. 4,269,605 to Dean et al, (issued May 26, 1989).

After binding the dihydroxyboryl compound to the support, the support can be rinsed with buffer or water. If the biological sample to be assayed has red blood cells, a detergent or other red blood cell lysing agent may optionally be included in the rinse if the assay is to measure glycated hemoglobin. Suitable detergents for use as a red blood cell lysing agent include Triton X-100. The presence of lysing agent in the support may facilitate the lysing of red blood cells from a whole blood sample. Alternatively, the sample may be pretreated with the red blood cell lysing agent or the red blood cell lysing agent may be included in the first buffer.

III Configuration of Solid Support Matrix

Figure 6:
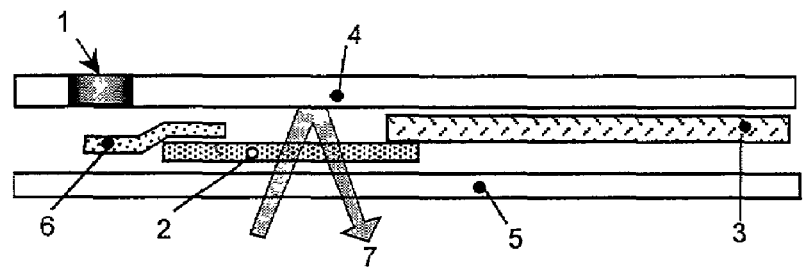
FIGS. 6A, 6B and 6C depict three strip configurations which may be used according to the methods of the present invention.
Figure 6:
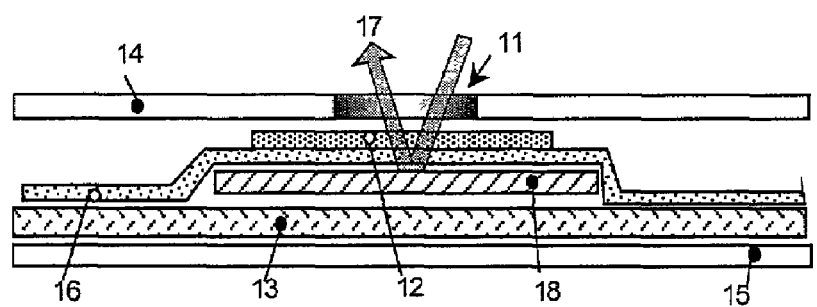
Figure 6C:
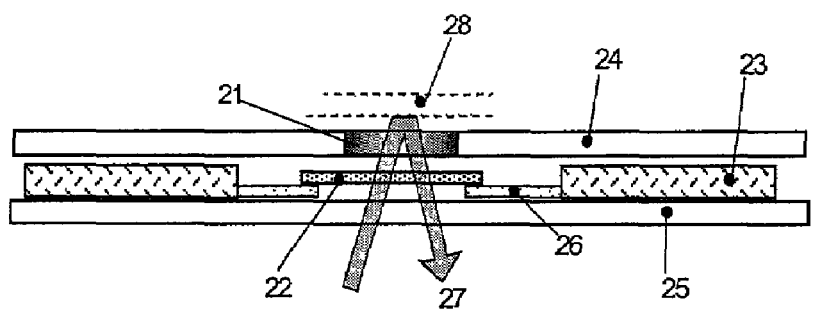

According to one aspect of the present invention, the solid support matrix is placed in a strip-type configuration along with other components to handle the flow of sample and buffer. The sample and buffers flow through the solid support matrix where binding occurs, and then into an absorbent material which will soak up the excess solution, allowing adequate volumes of buffer to pass through. Flow of solution through the strip can be along the length of the solid support matrix as in a lateral flow device, or through the thickness of the solid support, as in a vertical flow device (examples of such strip configurations are depicted in FIGS. 6A, 6B and 6C).

Suitable materials for use in the solid support include, for example, cellulose (including cellulose paper), nitrocellulose, cellulose acetate, polyacrylamide. agarose polyacrylamide copolymer, agarose, starch, nylon, nylon polyester, dextran, cross-linked dextran, dextran acrylamide copolymer, cross-linked hydroxyethylmethacrylate substituted cross-linked polystyrenes, polyvinylalcohol, wool, metal oxides, porous ceramics coated with hydrophilic organic polymers and glass.

IV The Sample and Preferred Buffers

Suitable biological samples for use according to the methods of the present invention include whole blood, serum and plasma. Red blood cells can be removed from the sample if desired by use of methods described in the art. Included are such methods using glass fibers (U.S. Pat. No. 4,477,575 issued Oct. 16, 1984 to Vogel et al.), carrier containing carbohydrate (U.S. Pat. No. 4,678,757 issued Jul. 7, 1987 to Rapkin) or a matrix containing a polyol (U.S. Pat. No. 5,725,774 issued Mar. 10, 1998 to Neyer).

According to a preferred aspect (especially for quantitation of non-hemoglobin glycated protein), the sample can be pretreated with a protein specific binding agent such as "dye" to label proteins and which may facilitate measurement of their concentration. A variety of such dyes known to those skilled in the art may be utilized with the method of the present invention. For example, a fluorescent dye such as fluorescein isothiocyanate ("FITC") may be used.

The sample is added to the solid support and allowed to flow through the support. The flow can be through the length of the support or through the thickness. The volume of sample added can range from a volume just large enough to cover the measurement area uniformly (such as about 3 to 5 μL) to a volume that will pass through the support in a reasonable time (approximately 40 μL). The actual volume limits will depend on the dimensions of the solid support and the other strip components. A larger (wider or longer) strip will be able to handle larger volumes of sample, but will require larger minimum volumes to cover the measurement area. A smaller strip will function with small volumes, but will not be able to handle large volumes.

After the sample has been absorbed into the strip, the first buffer is added. The pH of the first buffer is preferably between about 5.0 and about 7.0. More preferably, the pH of the first buffer is about 5.5 to about 7.0 for quantitation of glycated hemoglobin and about 5.0 to about 6.5 for quantitation of glycated albumin. The buffer contains a suitable buffering agent which has a pKa appropriate for control of the pH within the given range, but that does not otherwise affect the binding of the protein. Buffering agents suitable for use in the first buffer are known to those of skill in the art. Preferred buffering agents for use in the first buffer include MES, MOPS and HEPES. The buffering agent is present in a concentration sufficient to maintain the pH in the desired range. Suitable concentrations for the buffering agent may range from about 5 mM to about 500 mM. If the biological sample includes red blood cells, the buffer may further comprise a cell lysing agent such as, for example, Triton X-100 or Igepal CA-630. The buffer volume added can be standardized to a specific number of drops adequate to rinse through excess, non-bound sample. The adequacy of rinsing can also be monitored by the reflectance meter taking multiple measurements with the final measurement taken when the change is essentially zero.

The second buffer preferably has a pH from about 8.0 to about 10.0. The second buffer contains a suitable buffering agent which has a pK appropriate for control of pH within the given range, but that does not interfere with the binding of glycated protein to the immobilized dihydroxyboronate compound. Buffering agents suitable for use in the second buffer are known to those of skill in the art. Preferred buffering agents for use in the second buffer include ammonium acetate and taurine. The buffering agent is present in a concentration sufficient to maintain the pH in the desired range. Suitable concentrations for the buffering agent may range from about 5 mM to about 500 mM, or, alternatively, up to the solubility limit of the buffering agent. The adequacy of rinsing can be monitored as described for the first buffer. Optionally, the buffer can contain a divalent metal ion such as $Mg^{++}$ to help stabilize the binding of the protein to the boronate.

V Quantitation

The amount of protein bound to the support after each rinse can be quantitated using measurement methods known to those skilled in the art including measurement of optical absorbance or reflectance at an appropriate wavelength.

According to a preferred aspect of the method, a first reflectance measurement is made of the solid support after sample is added and the excess is rinsed through using the first buffer. This reflectance measurement is used in calculating the total protein concentration using an algorithm derived from calibration data or using "K/S" values as values proportional to concentration. A second reflectance measurement is made after washing off the non-glycated protein from the solid support using the second buffer. This measurement is used to calculate the glycated protein concentration in the same way as the first measurement. The percent glycated protein is calculated as the ratio of the glycated protein concentration to the total protein concentration×100.

Figure 7:
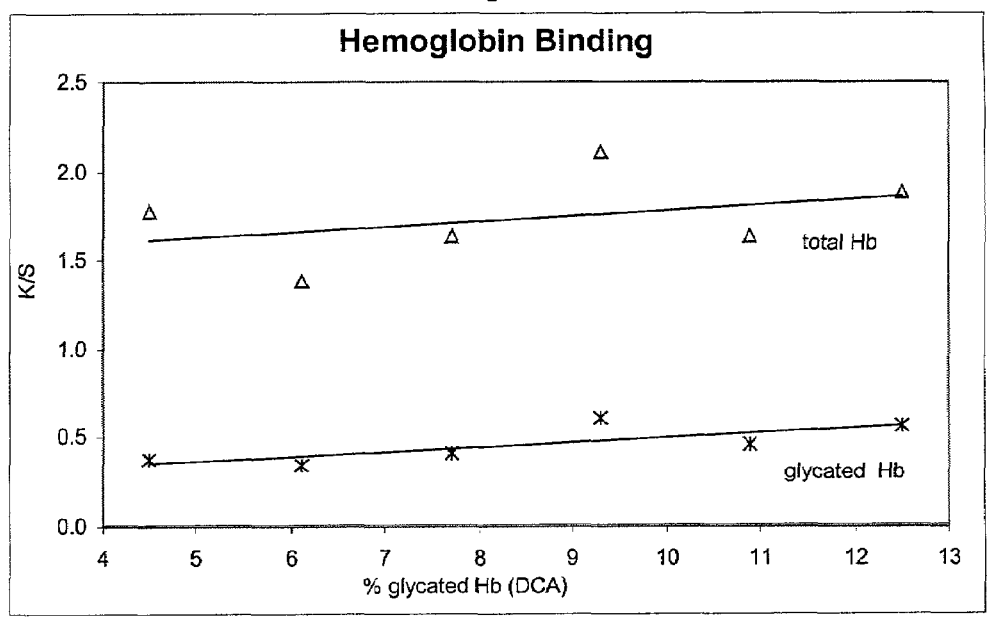
FIG. 7 depicts a graph of K/S vs. percent glycated hemoglobin ("Ж") showing proportionality of present invention assay results to the concentration of glycated hemoglobin in the sample in a strip assay format using the method of the present invention (open triangles depict total hemoglobin).
Figure 8:
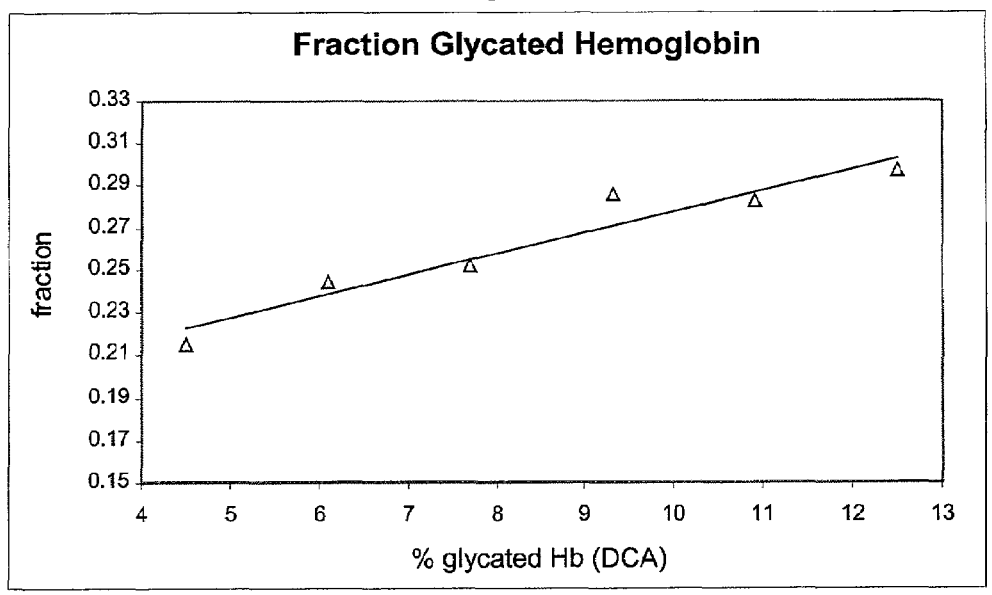
FIG. 8 depicts a graph of K/S fraction of glycated hemoglobin (glycated hemoglobin divided by total hemoglobin) vs. percent glycated hemoglobin showing proportionality of the fraction to glycated hemoglobin concentration in the sample in a strip assay format using the method of the present invention.

When light enters a transparent media, some of it is absorbed and some passes through the media. The Beer-Lambert law provides that the amount of light absorbed ("A") is the product of the concentration of the material absorbing the light ("C") and the length the light travels through the media ("d") (i.e. A=ecd, wherein e is the extinction coefficient of the absorbing material). When light enters a solid, the amount that reflects off the solid is determined by what is absorbed by the solid and what is scattered by the solid. The model used to define this relationship is the Kubelka-Munk Theory. This model defines two differential equations for the change in the light intensity as it passes into the solid and as it is scattered back out of the solid. The equations include the symbol "K" which is the absorption coefficient in solid phase and the symbol "S" which is the scattering coefficient. In the simplified derivation, the equations reduce to the following: $K/S=[(1-R)^2]/(2R)$ where R is the measured reflectance and K/S is proportional to the concentration of the absorbing/scattering material. In certain of the Figures (see, e.g., FIGS. 7 and 8) the data taken using the reflectance meter are plotted with y values of K/S which are proportional to the concentration of the analyte.

The methodology used in the assay is adaptable for use in a strip that can be used with hand held reflectance meters used in glucose assays.

The total amount of protein that binds to the solid support is controlled by the binding capacity of the negatively charged groups immobilized on the support. We have observed that glycated and non-glycated protein rapidly bind to the derivatized support in the same ratio as in the sample. The volume of sample added to the support does not have to be measured since any excess will be rinsed through.

The reported percent glycation is calculated from the ratio of two measurements made at the same location on the solid support in the strip. Therefore, variations in the total amount of protein bound by different strips will not affect the reported result. Since both total and glycated protein are measured using the same method at the same location on the solid support, variations which could affect the measurements will have the same effect on both measurements, minimizing "noise".

To assist in understanding, the present invention will now be further illustrated by the following examples. These examples, as they related to the present invention, should not, of course, be construed as specifically limiting the invention. Also, such variations of the invention, now known or later developed, which would be within the purview of one skilled in the art are considered to fall within the scope of the present invention, as described herein and herein after claimed.

EXAMPLES

Example 1

Preparation of the Boronated Solid Support Matrix

According to a preferred aspect of the detection method of the present invention, a solid support matrix suitable for use in a strip configuration is prepared by covalently attaching a derivative of boronate, m-aminophenylboronate to a carboxy cellulose based material using a conventional linking chemistry.

Materials
1. Solid Support Matrix: cellulose based solid with carboxylic acid groups covalently bound (Sartobind C membrane, Sartorious).
2. EDC (1-ethyl-3-(3-dimethylaminopropyl)carbodiimide hydrochloride) (Pierce)
3. Boronate derivative: m-aminophenylboronic acid (Sigma-Aldrich)
4. Buffer: 0.1M MES buffer, pH 6.5

Procedure

A 46.7 mg portion of m-aminophenylboronate is dissolved in 25 mL of 100 mM MES buffer. The pH is re-adjusted to 6.5 after the boronate dissolves. A 28.9 mg portion of EDC is dissolved in the MES-boronate solution. The solid support matrix is soaked in the solution for the desired time (25 mL of solution was enough to treat a 30 cm$^2$ piece of matrix). The matrix is removed from the solution and rinsed in the MES buffer and allowed to air dry.

The binding characteristics of the boronated solid support matrix prepared as above using different soak times were measured using the elution assay described in Example 2. The resulting binding of total (open triangles) and glycated hemoglobin (closed triangles) is depicted in FIG. 1. Open circles show the ratio of glycated to total hemoglobin.

As more boronate groups are added to the solid support matrix, fewer carboxylic groups are left for ionic binding. The ratio of glycated hemoglobin to total hemoglobin increases until there is a sufficiency of boronate groups, then the ratio remains the same even through the total binding is decreased.

Example 2

Effect of Variable Incubation Times

An assay using the boronated support of Example 1 in a single measurement assay ("Single Measurement Method") was compared to a method of the present invention to determine the effect of variable incubation times on the concentration results obtained with each method.

The following assays were performed to compare the two methods. In the Single Measurement Method assay, blood lysate samples from a non-diabetic individual and a diabetic individual were diluted 1:1 with 500 mM ammonium acetate buffer pH=9.5 with 50mM $Mg_{++}$ and the samples were allowed to be in contact with the boronated solid support matrix prepared as in Example 1 for a variety of time periods. Following incubation, the boronated solid supports were rinsed with ammonium acetate buffer pH=9.5. Glycated hemoglobin was eluted with an elution buffer comprised of tris buffer at pH 8.0 containing 200mM sorbitol. The absorbance of the eluent was measured at 415 mM.

Figure 2:
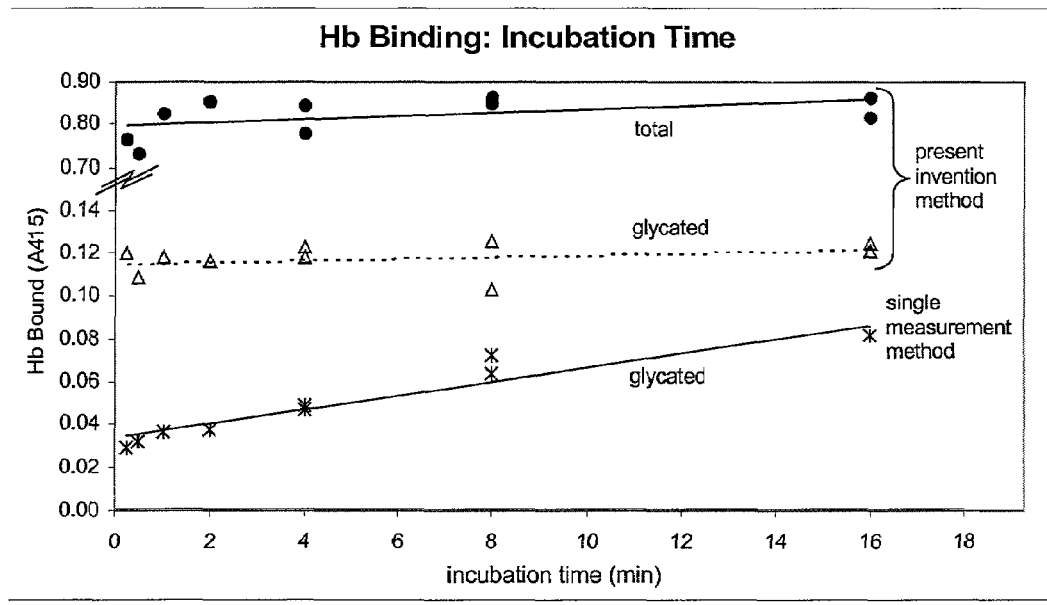
FIG. 2 depicts a graph of optical absorbance of bound hemoglobin at 415 nm vs. incubation time for blood lysate of a diabetic sample comparing a single measurement assay ("Ж" for glycated) to the method of the present invention (circles for total Hb, open triangles for glycated Hb).
Figure 3:
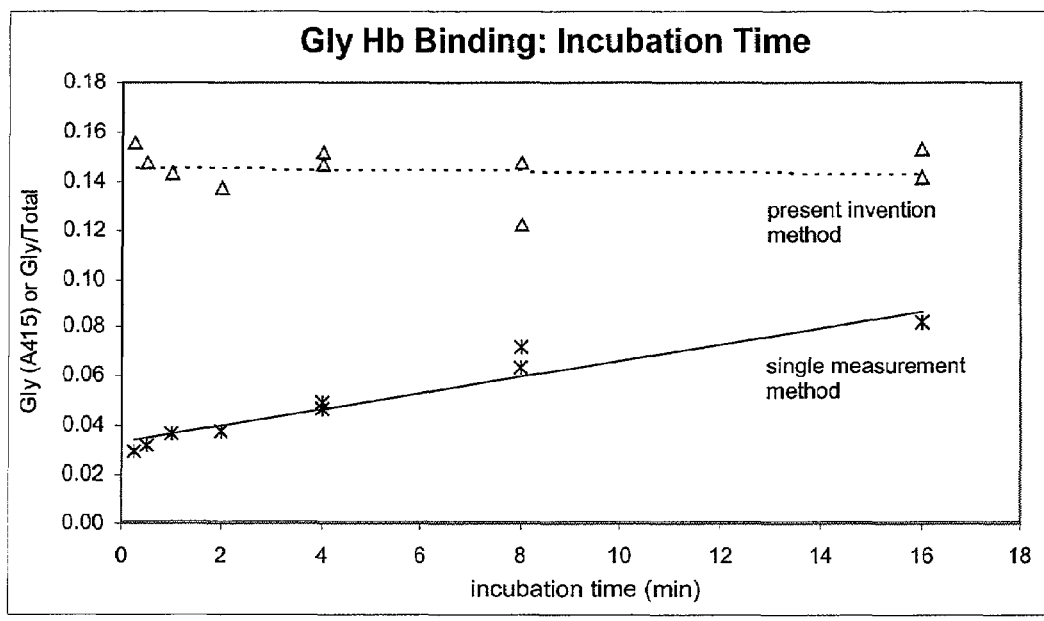
FIG. 3 depicts a graph of optical absorbance at 415 nm of glycated hemoglobin or fraction of glycated hemoglobin vs. incubation time for blood lysate of a diabetic sample comparing a single measurement assay (adapting the method of published PCT application WO 98/40750 "Ж") to the method of the present invention (open triangles).

In the second assay, corresponding to the method of the present invention, blood lysate samples from a non-diabetic individual and a diabetic individual were diluted 1:1 with mM MES buffer pH=6.5. The samples were allowed to be in contact with the boronated solid support matrix for time periods identical to those used for the first assay and were incubated at a similar time periods as done with the first assay. Following incubation the diluted samples were discarded and the boronated solid supports were rinsed with MES buffer pH=6.5. The solid support matrixes were then rinsed a second time with 500 mM ammonium acetate buffer pH=9.5 containing 50 mM $Mg^{++}$. The absorbance of the rinse was measured at 415 nm corresponding to non-glycated hemoglbin. Glycated hemoglobin was eluted off the matrix and the absorbance of this rinse was measured. The data obtained from the diabetic sample is provided in the Table I (see also FIGS. 2 and 3).

TABLE I

| | Diabetic blood lysate sample | | | |
|---|---|---|---|---|
| dwell | Present Invention | | | Single Measurement |
| time (min) | total | gly | Gly/total | Gly |
| 0.25 | 0.769 | 0.12 | 0.156 | 0.029 |
| 0.5 | 0.739 | 0.109 | 0.147 | 0.032 |
| 1 | 0.824 | 0.118 | 0.143 | 0.037 |
| 2 | 0.846 | 0.116 | 0.137 | 0.038 |
| 4 | 0.838 | 0.123 | 0.147 | 0.047 |

TABLE I-continued

Diabetic blood lysate sample

| dwell | Present Invention | | | Single Measurement |
|---|---|---|---|---|
| time (min) | total | gly | Gly/total | Gly |
| 8 | 0.856 | 0.126 | 0.147 | 0.072 |
| 16 | 0.814 | 0.125 | 0.154 | 0.082 |
| 4 | 0.779 | 0.118 | 0.151 | 0.049 |
| 8 | 0.844 | 0.103 | 0.122 | 0.064 |
| 16 | 0.857 | 0.121 | 0.141 | 0.082 |

Linear regression analysis of this data clearly showed, that the results obtained using the single measurement method were heavily dependent on incubation time. However, when using the methods of the present invention the results obtained were independent of incubation time, which it is believed will provide more reliable results and make the assay more robust and suitable for untrained users.

Example 3

Effect of pH on Binding

Figure 4:
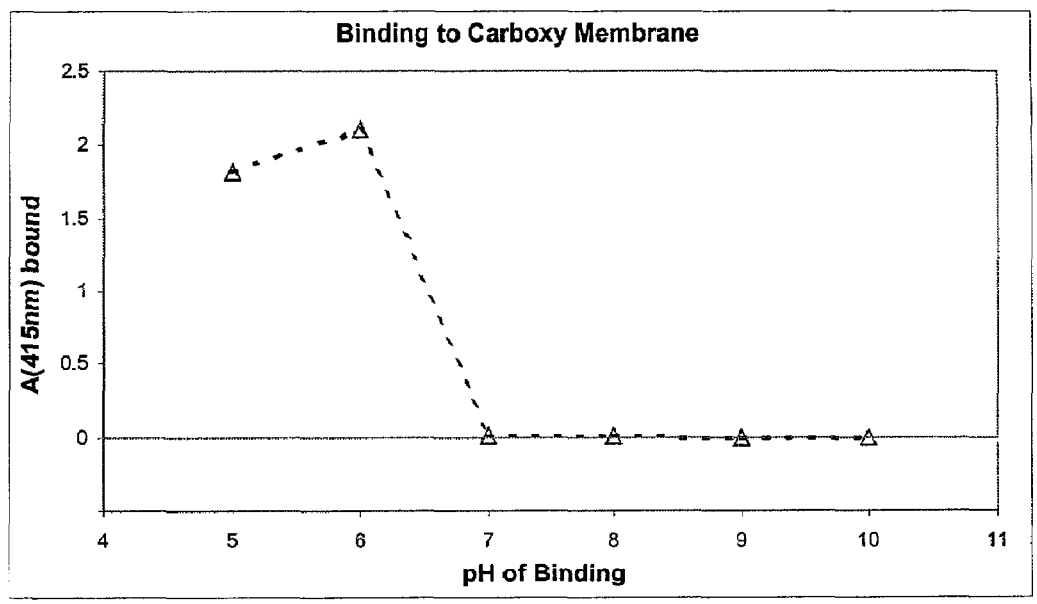
FIG. 4 depicts a graph of the absorbance of hemoglobin binding to the carboxy cellulose support (no added boronate groups) over a pH range.

The pH of the buffer affects the amount of hemoglobin binding to the boronated support. If the pH is low, then both glycated and non-glycated hemoglobin are bound. If the pH is high, only glycated hemoglobin will bind. FIG. 4 depicts the binding of hemoglobin to the carboxy cellulose membrane (no boronate groups present) following the assay procedure described in Example 2. The membrane loses its ionic binding of hemoglobin between pH 6 and 7 when boronate is not present.

Figure 5:
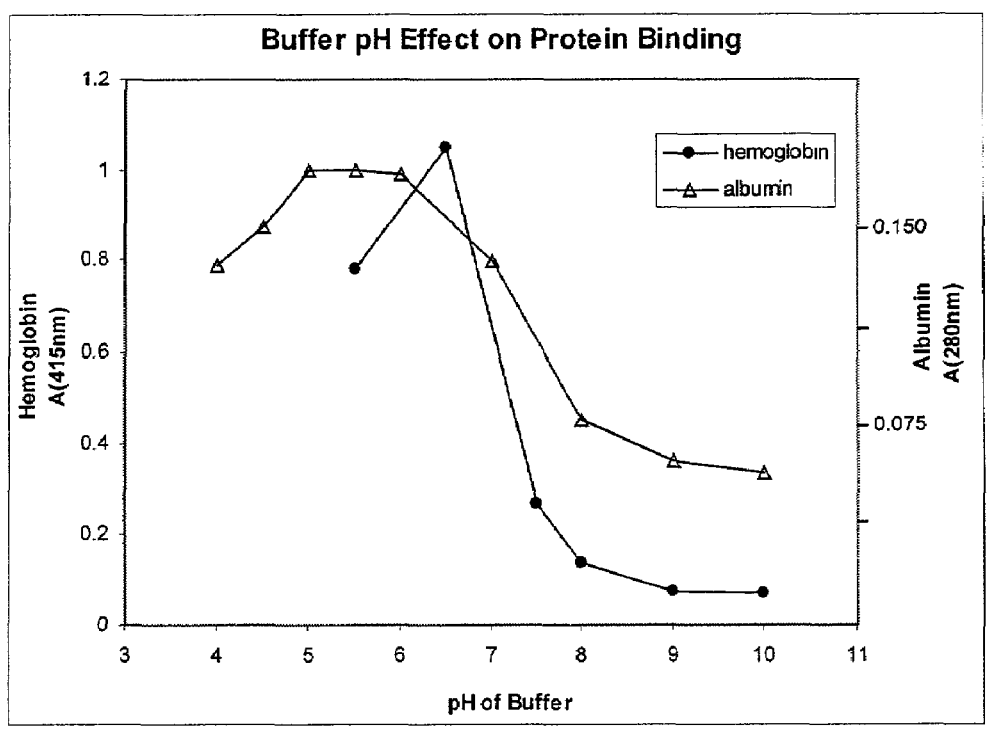
FIG. 5 depicts a graph of the absorbances of hemoglobin (closed circles) and of albumin (open triangles) bound to the boronated support over a pH range.

FIG. 5 depicts the hemoglobin and human serum albumin binding properties of the carboxy cellulose support with added boronate groups, prepared as described in Example 1. Binding of the protein occurs at lower pH's due to the negatively charged carboxyl groups. The protein bound at the higher pH, due to the phenylboronate, is the glycated protein present in the samples.

Example 4

Description of Exemplary Strip Design Configurations

The boronated solid support matrices containing negatively charged groups can be incorporated in any assay where the separation of glycated from non-glycated protein is required. According to the preferred assay methods of the present invention the boronated solid support matrix is used in combination with other components to direct the flow of the sample and buffers. These components may be in the form of a strip which can be placed into a small, hand held reflectance meter for quantitation. Suitable alternative configurations for the strip are depicted in FIGS. 6A, 6B and 6C.

In the lateral flow strip configuration (FIG. 6A), the fluids move through the length of the boronated support (parallel to the surface of the support). In the vertical flow (FIG. 6B) and combination strip configuration (FIG. 6C), the movement of fluid is more through the thickness of the solid support matrix (perpendicular to the surface).

Each configuration depicted has a sample application site (1, 11 or 21) which is a hole in a piece of plastic (normally white for appearances), (4, 14 or 24). The boronated solid support (2, 12 or 22) is in contact with wicking material (6, 16 or 26). In the configuration depicted in FIG. 6A, fluids flow from the application area (1) through the wicking material (6) to the support (2) and through the support to the reservoir (3). In the configurations depicted in FIGS. 6B and 6C, fluids flow from the application area (11 or 21) and boronated support (12 or 22) to the wicking material (16 or 26) and the reservoir (13 or 23). All the components are placed on top of the bottom piece of plastic, either white (15) or clear (5 or 25) depending on the configuration. The reflectance of the boronated support is measured by shining a light of the selected wavelength onto the support surface and measuring its intensity (7, 17 or 27). In the configurations depicted in FIGS. 6B and 6C, there is a piece of white reflecting material (18 or 28) placed behind the support to reflect light passing through the support back through it to reduce loss of intensity.

Example 5

Assay Proportionality: Glycated Hemoglobin

A vertical flow strip design described in Example 4 and as depicted in FIG. 6D was used in assays of mixtures of blood lysates from normal and diabetic blood samples. Approximately 8 μl of blood lysate was deposited on the boronated solid support matrix prepared as in Example 1. The application site was then rinsed with ~50 μL MES buffer pH=6.5 (100 mM) and a reflectance measurement at 430 nm was recorded. The application site was then rinsed with ~50 μL ammonium acetate buffer (500 mM) pH=9.5, containing 50 mM $Mg^{++}$ and a second reflectance measurement at 430 nm was recorded at the application site. The reflectance values were converted to K/S values which are proportional to the concentration of hemoglobin being measured. The data are shown in Table II below (see FIGS. 7 and 8).

TABLE II

| | | Reflectance | | k/s | | |
|---|---|---|---|---|---|---|
| norm.:diab. | % gly hb* | Total | gly | Total | gly | ratio (gly/total) |
| 1:0 | 4.5 | 0.186 | 0.428 | 1.781 | 0.382 | 0.215 |
| 4:1 | 6.1 | 0.219 | 0.448 | 1.393 | 0.340 | 0.244 |
| 3:2 | 7.7 | 0.197 | 0.415 | 1.637 | 0.412 | 0.252 |
| 2:3 | 9.3 | 0.165 | 0.350 | 2.113 | 0.604 | 0.286 |
| 1:4 | 10.9 | 0.197 | 0.395 | 1.637 | 0.463 | 0.283 |
| 0:1 | 12.5 | 0.179 | 0.363 | 1.883 | 0.559 | 0.297 |

The regression statistics of the data plots are shown in the Table III below.

TABLE III

| plot | Slope | intercept | $S_{y \cdot x}$ | CV* |
|---|---|---|---|---|
| Total Hb | 0.031 | 1.48 | 0.255 | 14.7 |
| Glycated Hb | 0.026 | 0.24 | 0.076 | 15.9 |
| Gly/total | 0.010 | 0.18 | 0.010 | 3.8 |

*calculated using the mean values for each fraction

The plots, $S_{y \cdot x}$ and resulting C.V.'s show that the total and glycated values measured vary from strip to strip. However, the large variations are reduced when the ratio of the two values is taken, demonstrating the advantage of using the methods of the present invention.

The results show that the calculated glycated fraction is proportional to the percent glycated hemoglobin in the sample.

The term CV is the coefficient of variation and is the measure of the scatter of replicate measurements around a mean value. The coefficient is calculated from the standard deviation ("SD") and the mean value ("M") of the replicates (i.e. CV=100×SD/M). The benefit to using this value is that because it is expressed as a percentage it may be compared to other CV values without the requirement of knowing the mean values.

The term $S_{y,x}$ is a measure of variability used in linear regression calculation. It is the measure of the variability of "y" after removing the effect of "X" (i.e. it measures the variability of the data around the regression line).

Example 6

Assay Proportionality: Glycated Protein

A normal albumin sample was obtained from serum from a non-diabetic individual. An elevated glycated albumin sample was prepared from human serum albumin glycated in vitro (see, U.S. Pat. No. 5,589,393 to Michael D. Fiechtner, et al., issued Dec. 31, 1996).

Figure 9:
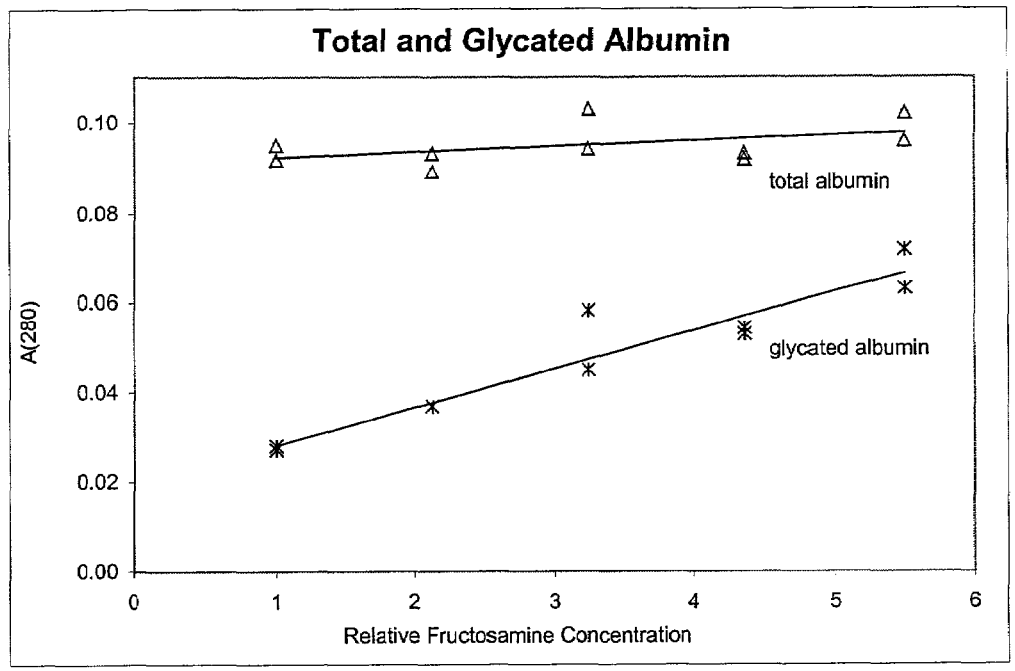
FIG. 9 depicts a graph of optical absorbance at 280 nm for total (open triangles) and glycated albumin ("Ж") vs. relative fructosamine content (proportional to fractional amount of glycated albumin) in a sample.
Figure 10:
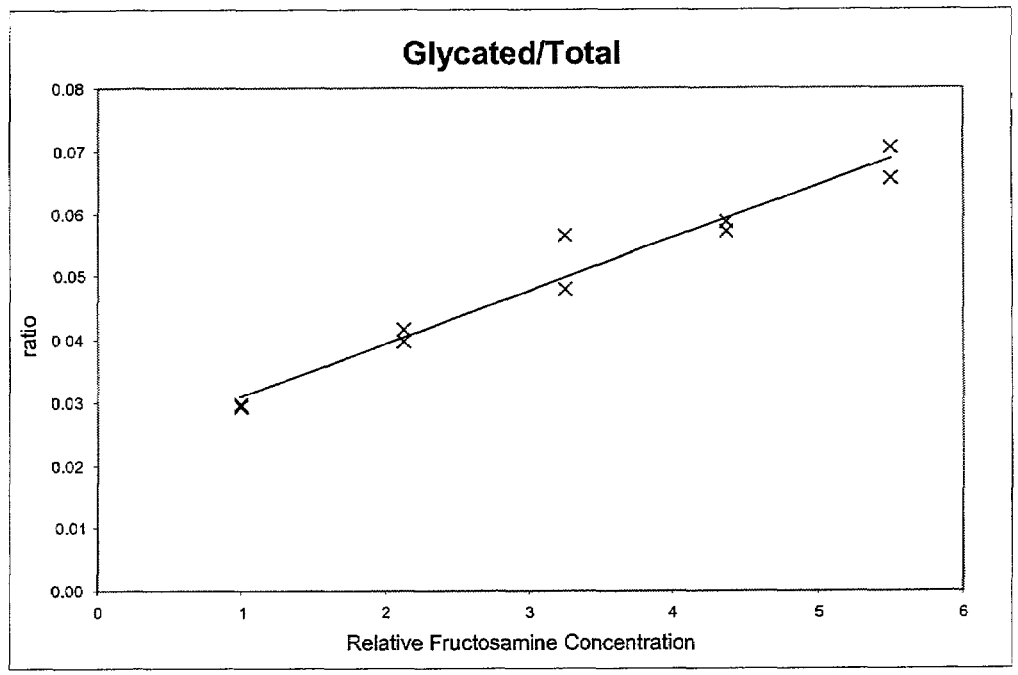
FIG. 10 depicts a graph of the ratio of glycated albumin to total albumin (absorbance at 280 nm) vs. relative fructosamine content (proportional to the fractional amount of glycated albumin) in a sample.

Both samples were assayed for fructosamine amount using a manual fructosamine assay based on Tietz, *Textbook of Clinical Chemistry*, 2nd Ed. (W. B. Saunders Co., Carl A. Burtis, Edward Ashwood, Eds., 1994), page 986–988. The elevated glycated albumin sample was found to contain 5.5 times the concentration of fructosamine as the normal albumin sample. The samples were mixed together in the proportions shown in Table IV (see also, FIGS. 9 and 10).

The resulting samples were assayed in accordance with the present invention as described in Example 2 and the A280 absorbance values recorded in Table IV.

TABLE IV

| Relative Fructosamine Conc. | measured total-gly | Measured glycated | calculated total | gly/total |
|---|---|---|---|---|
| 1.0 | 0.065 | 0.027 | 0.092 | 0.029 |
| 1.0 | 0.067 | 0.028 | 0.095 | 0.029 |
| 2.1 | 0.056 | 0.037 | 0.093 | 0.040 |
| 2.1 | 0.052 | 0.037 | 0.089 | 0.042 |
| 3.3 | 0.045 | 0.058 | 0.103 | 0.056 |
| 3.3 | 0.049 | 0.045 | 0.094 | 0.048 |
| 4.4 | 0.040 | 0.053 | 0.093 | 0.057 |
| 4.4 | 0.038 | 0.054 | 0.092 | 0.059 |
| 5.5 | 0.033 | 0.063 | 0.096 | 0.066 |
| 5.5 | 0.030 | 0.072 | 0.102 | 0.071 |

Regression statistics for the above plot are given in the Table V below.

TABLE V

| Fraction | slope | Intercept | $R^2$ |
|---|---|---|---|
| total | 0.001 | 0.091 | 0.177 |
| glycated | 0.009 | 0.020 | 0.908 |
| gly/total | 0.008 | 0.022 | 0.962 |

The calculated glycated albumin fraction was observed to be proportional to the fructosamine content. The results are proportional from the low sample concentration to 5.5 times the low concentration as shown by the regression statistics of $R^2$. Therefore the assay method used to measure glycated hemoglobin is also suitable for the measurement of glycated albumin.

Example 7

Effect of Sample Volume

Figure 11:
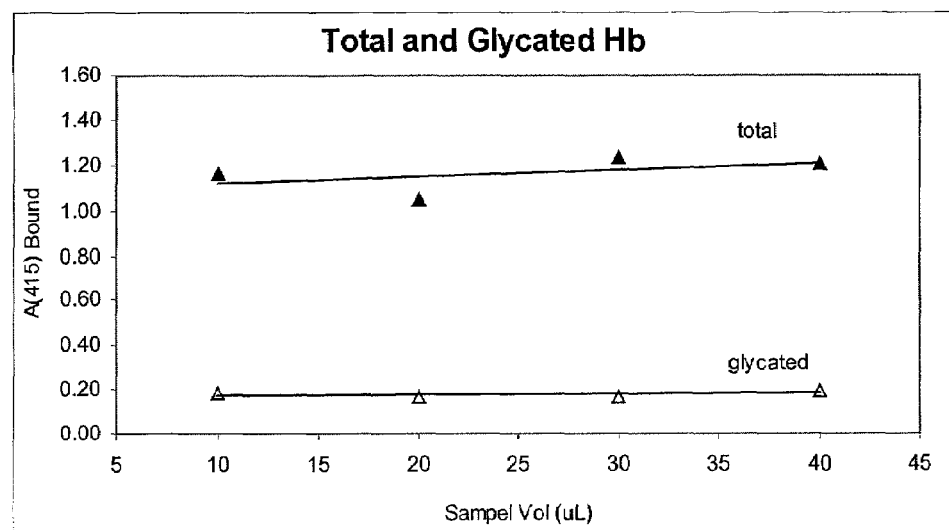
FIG. 11 depicts a graph of optical absorbance at 415 nm of bound total hemoglobin (closed triangles) and glycated hemoglobin (open triangles) vs. whole blood sample volume in a lateral flow device. (See FIG. 6A)
Figure 12:
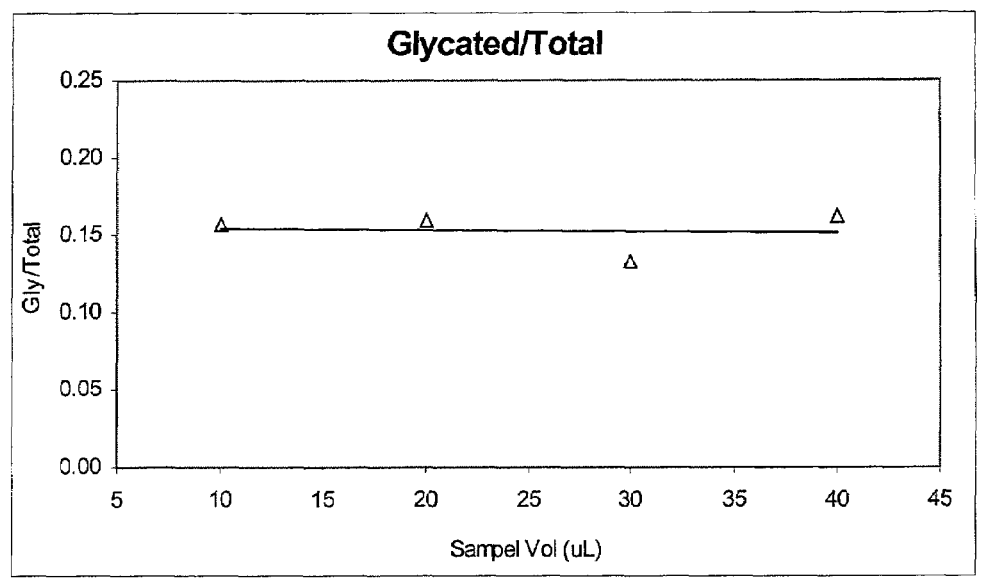
FIG. 12 depicts a graph of the ratio of glycated hemoglobin divided by total hemoglobin vs. whole blood sample volume in a lateral flow device. (See FIG. 6A)

A lateral flow strip format as described in Example 4 and depicted in FIG. 6A was used to assay non-diabetic and diabetic whole blood at varied sample volumes to determine the effect of sample volume on the assay, which followed the method described in Example 2. The measured absorbance values (415 nm) are presented in the Table VI (see FIGS. 11 to 12).

TABLE VI

| | absorbance (415) | | |
|---|---|---|---|
| μL sample | total Hb | Gly Hb | gly/total |
| 10 | 1.164 | 0.183 | 0.157 |
| 20 | 1.053 | 0.167 | 0.159 |
| 30 | 1.233 | 0.164 | 0.133 |
| 40 | 1.206 | 0.195 | 0.162 |

The regression statistics are shown in the Table VII.

TABLE VII

| Fraction | slope | Intercept | $S_{y,x}$ | slope = 0? |
|---|---|---|---|---|
| Total Hb | 0.0031 | 0.088 | 0.084 | yes (P = 0.502) |
| gly Hb | 0.0003 | 0.169 | 0.017 | yes (P = 0.706) |
| Gly/total | −0.0001 | 0.156 | 0.016 | yes (P = 0.893) |

The results demonstrate that binding of total hemoglobin and glycated hemoglobin in the assay are independent of sample volume when the volume ranges from about 10 μL to about 40 μL in assays of whole blood.

Example 8

Effect of Variation of Total Hemoglobin Concentration

Figure 13:
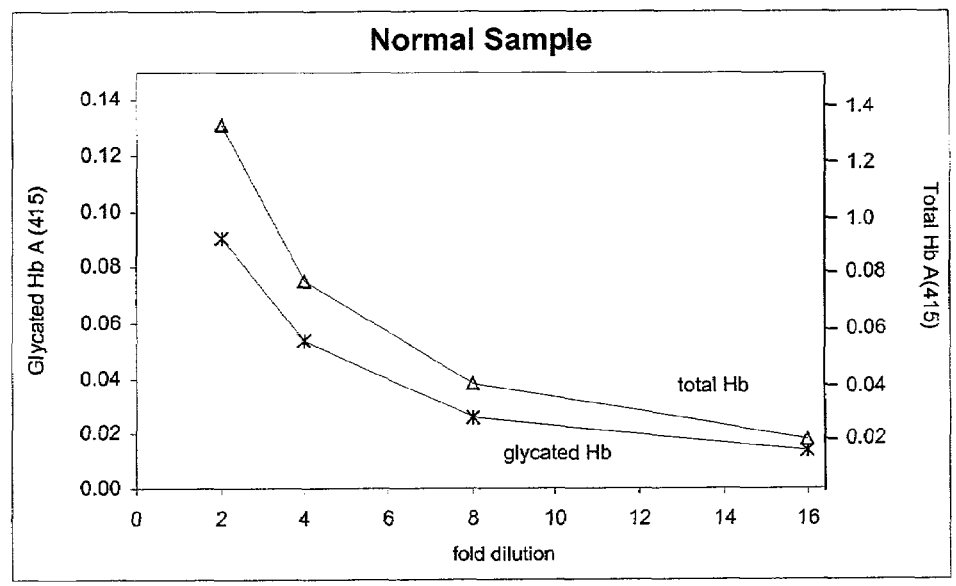
FIG. 13 depicts a graph of optical absorbance at 415 nm of total hemoglobin (open triangles) and glycated hemoglobin ("Ж") vs. dilution of a normal blood sample lysate.
Figure 14:
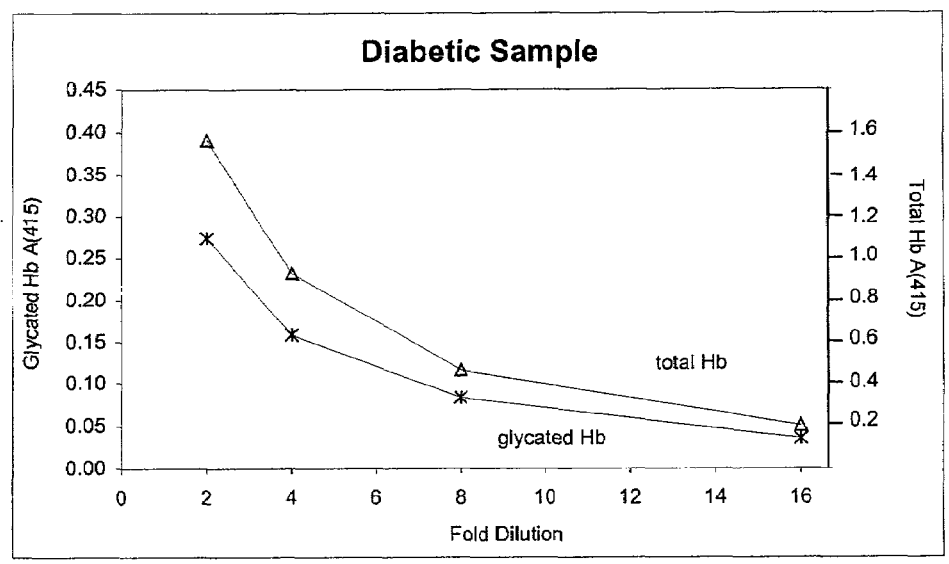
FIG. 14 depicts a graph of optical absorbance at 415 nm of total hemoglobin (open triangles) and glycated hemoglobin ("Ж") vs. dilution of a diabetic blood sample lysate.
Figure 15:
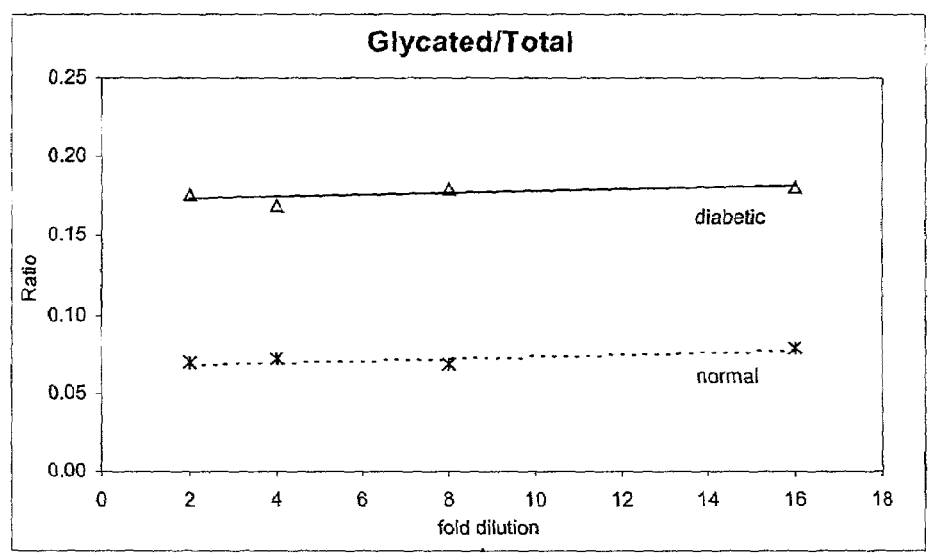
FIG. 15 depicts a graph of optical absorbance at 415 nm of glycated hemoglobin divided by total hemoglobin vs. dilution of a normal ("Ж") and diabetic blood (open triangles) sample lysate.

The effect of varying the amount of total hemoglobin in the assay was determined using the assay procedure described in Example 2 to assay diluted blood samples. Table VIII below list the absorbance values (415 nm) from the assays of non-diabetic and diabetic blood lysates diluted by factors of 2, 4, 8 and 16 (see FIGS. 13 to 15).

TABLE VIII

| Sample | dil factor | A (415 nm) | | % gly |
|---|---|---|---|---|
| | | Total Hb | gly | |
| Normal | 2 | 1.309 | 0.091 | 6.9 |
| | 4 | 0.754 | 0.054 | 7.2 |
| | 8 | 0.382 | 0.026 | 6.8 |
| | 16 | 0.178 | 0.014 | 7.9 |
| Diabetic | 2 | 1.561 | 0.275 | 17.6 |
| | 4 | 0.929 | 0.157 | 16.9 |
| | 8 | 0.467 | 0.084 | 18.0 |
| | 16 | 0.199 | 0.036 | 18.1 |

The regression statistics are listed in the Table IX below for the graphs.

TABLE IX

| sample | slope | Intercept | $S_{y.x}$ | slope = 0? |
|---|---|---|---|---|
| normal | 0.00060 | 0.067 | 0.0035 | yes (P = 0.202) |
| Diabetic | 0.00058 | 0.172 | 0.0049 | yes (P = 0.329) |

The amounts to total hemoglobin and glycated hemoglobin that bind to the solid support matrix decrease with decreasing total hemoglobin concentration. The calculated glycated hemoglobin/total hemoglobin, however, was constant over the dilutions assayed as seen in the regression statistics (i.e. slopes are essentially zero). This demonstrated the advantage of the methods of the present invention (i.e. using the ratio of two measurements to produce results independent of sample dilution or hemoglobin concentration).

Example 9

Comparison to Other Commercial Assays

Twenty-five whole blood samples were assayed using the strip configuration depicted in FIG. 6C, and described in Example 4 and following the assay method described in Example 5. The samples were also assayed using two commercially available tests for hemogoblin A1c.

The commercially available tests compared to the method of the present invention were:

1. Roche Integra 400 (Roche Diagnostics)

The assay was performed by a desktop, multi-sample analyzer using an immunoturbidimetric determination of the glycated N-terminal valine of the β-chain in hemoglobin or HbA1c according to the manufacturer's instructions. Each sample was assayed once by this method.

2. DCA 2000 (Bayer)

The assay was performed by a desktop, single assay analyzer using an immunoturbidimetric determination of HbA1c according to the manufacturer's instructions. Each sample was assayed once using this assay.

Figure 16:
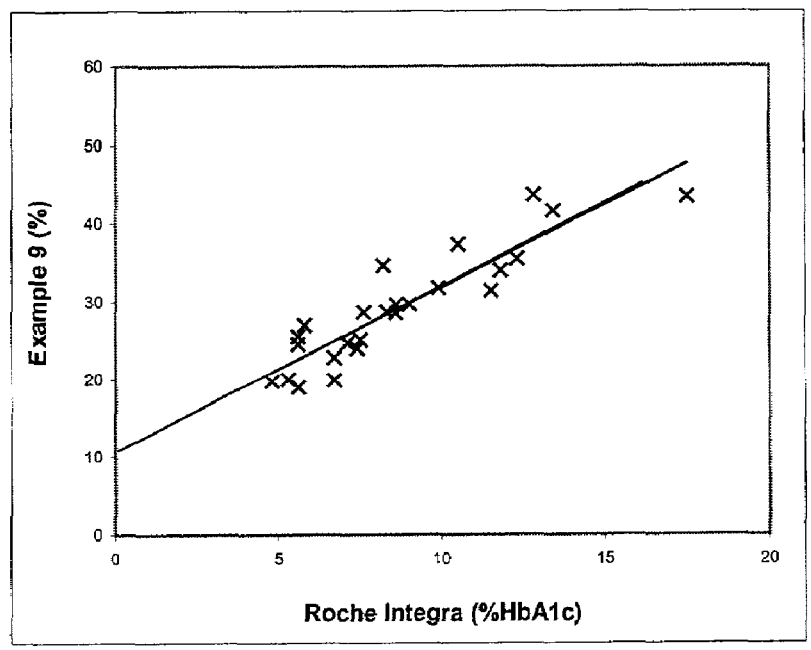
FIGS. 16A and 16B depict graphs showing correlation between whole blood assay results using an assay of the present invention and two other commercially available assays for hemoglobin A1c.
Figure 16:
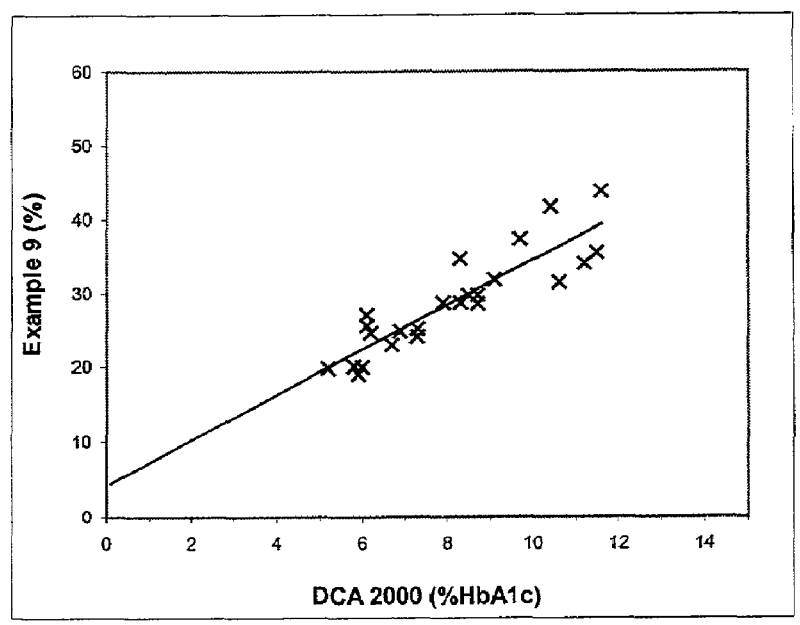

The results are plotted in FIGS. 16A and 16B and show that the results obtained using the compared methods and the methods of the present invention correlate.

We claim:

1. A method for determining a ratio of an amount of a glycated form of a protein to a total amount of the protein in a sample containing both glycated and nonglycated forms of the protein, comprising:
   providing a solid support having negatively charged carboxyl groups immobilized thereon, which groups are capable of binding both the glycated and the nonglycated forms of the protein at a first pH, said support also having hydroxyboryl groups immobilized thereon, interspersed with the negatively charged carboxyl groups, which hydroxyboryl groups are capable of binding the glycated form of the protein at a second pH;
   adding the sample to the solid support at the first pH, thereby binding both the glycated and the nonglycated forms of the protein to the negatively charged carboxyl groups on the solid support, and then performing a first measurement indicative of the total amount of the glycated and the nonglycated forms of the protein bound to the solid support;
   changing the pH on the support to the second pH, thereby removing both the nonglycated form of the protein and the glycated form of the protein from the negatively charged carboxyl groups, after which removal the glycated form of the protein immediately binds to the hydroxyboryl groups on the support independent of incubation time, and then performing a second measurement indicative of the amount of the glycated form of the protein bound to the solid support; and
   determining the ratio of the amount of the glycated form of the protein to the total amount of the glycated and the nonglycated forms of the protein in the sample from the first and second measurements.

2. The method of claim 1, wherein the first pH is achieved by applying a buffer of about pH 5.0 to 7.0.

3. The method of claim 1, wherein the second pH is achieved by applying a buffer of about pH 8.0 to 10.0.

4. The method of claim 1, wherein the glycated protein is hemoglobin.

5. The method of claim 1, wherein the glycated protein is albumin.

6. The method of claim 1, wherein the sample comprises blood.

7. The method of claim 1, wherein the sample comprises serum.

8. The method of claim 1, wherein the sample comprises plasma.

9. The method of claim 1, wherein the first and second measurements measure an optical property of the protein.

10. The method of claim 1, wherein the first and second measurements are optical readings at a predetermined wavelength.

11. The method of claim 1, wherein the first and second measurements measure a protein label.

12. The method of claim 1, wherein the hydroxyboryl group is of the type

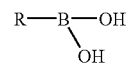

where R is selected from the group consisting of phenyl, alkyl of 1–6 carbons, ethyl, 1-propyl, 3-methyl-1-butyl and aminophenyl.

13. The method of claim 1, wherein the solid support is selected from the group consisting of cellulose, nitrocellulose, cellulose acetate, polyacrylamide, agarose polyacrylamide copolymer, agarose, starch, nylon, nylon polyesters, dextran, cross-linked dextran, dextran acrylamide copolymer, cross-linked hydroxyethylmethacrylate, substituted cross-linked polystyrenes, polyvinylalcohol, wool, metal oxides, porous ceramics coated with hydrophilic organic polymers and glass.

14. A method for determining a ratio of an amount of glycated albumin to a total amount of glycated and nonglycated albumin in a sample containing both glycated and nonglycated albumin, comprising:
   providing a strip-type device comprising:
   (1) a solid support matrix having a measurement area; and
   (2) negatively charged carboxyl groups and dihydroxyboryl groups immobilized and interspersed on the solid support matrix, said negatively charged carboxyl groups are capable of binding both glycated and nonglycated albumin at a first pH between about 5.0 and about 7.0, and said dihydroxyboryl groups are capable of binding glycated albumin at a second pH between about 8.0 and about 10.0;

adding the sample to the solid support matrix at the first pH, thereby binding both glycated and nonglycated albumin to the negatively charged carboxyl groups on the solid support matrix, and then performing a first optical measurement on the measurement area indicative of the total amount of glycated and nonglycated albumin bound to the solid support matrix;

changing the pH on the solid support matrix to the second pH, thereby removing both the nonglycated albumin and the glycated albumin from the negatively charged carboxyl groups, after which removal the glycated albumin immediately binds to the dihydroxyboryl groups on the solid support matrix independent of incubation time, and then performing a second optical measurement on the measurement area indicative of the amount of glycated albumin bound to the solid support matrix; and determining the ratio of the amount of glycated albumin to the total amount of glycated and nonglycated albumin in the sample from the first and second optical measurements.

15. The method of claim 14, wherein said dihydroxyboryl groups have the formula:

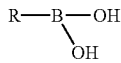

where R is selected from the group consisting of phenyl, alkyl of 1–6 carbons, ethyl, 1-propyl, 3-methyl-1-butyl and aminophenyl.

16. The method of claim 14, wherein the solid support matrix is selected from the group consisting of cellulose, nitrocellulose, cellulose acetate, polyacrylamide, agarose polyacrylamide copolymer, agarose, starch, nylon, nylon polyesters, dextran, cross-linked dextran, dextran acrylamide copolymer, cross-linked hydroxyethylmethacrylate, substituted cross-linked polystyrenes, polyvinylalcohol, wool, metal oxides, porous ceramics coated with hydrophilic organic polymers and glass.

17. The method of claim 16, wherein said solid support matrix is carboxy cellulose.

18. The method of claim 14, wherein said first pH is achieved with a buffer selected from the group consisting of MES, MOPS and HEPES.

19. The method of claim 14, wherein said second pH is achieved with a buffer selected from the group consisting of ammonium acetate or taurine.

20. The method of claim 14, wherein the sample comprises blood, plasma or serum.

21. A method for determining a ratio of an amount of glycated hemoglobin to a total amount of glycated and nonglycated hemoglobin in a sample containing both glycated and nonglycated hemoglobin, comprising:

providing a strip-type device comprising:
(1) a solid support matrix having a measurement area; and
(2) negatively charged carboxyl groups and dihydroxyboryl groups immobilized and interspersed on the solid support matrix, said negatively charged carboxyl groups are capable of binding both glycated and nonglycated hemoglobin at a first pH between about 5.0 and about 7.0, and said dihydroxyboryl groups are capable of binding glycated hemoglobin at a second pH between about 8.0 and about 10.0;

adding the sample to the solid support matrix at the first pH, thereby binding both glycated and nonglycated hemoglobin to the negatively charged carboxyl groups on the solid support matrix, and then performing a first optical measurement on the measurement area indicative of the total amount of glycated and nonglycated and nonglycated hemoglobin bound to the solid support matrix;

changing the pH on the solid support matrix to the second pH, thereby removing both the nonglycated hemoglobin and the glycated hemoglobin from the negatively charged carboxyl groups, after which removal the glycated hemoglobin immediately binds to the dihydroxyboryl groups on the solid support matrix independent of incubation time, and then performing a second optical measurement on the measurement area indicative of the amount of glycated homoglobin bound to the solid support matrix; and determining the ratio of the amount of glycated hemoglobin to the total amount of glycated and nonglycated hemoglobin in the sample from the first and second optical measurements.

22. The method of claim 21, wherein said dihydroxyboryl groups have the formula:

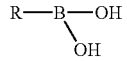

where R is selected from the group consisting of phenyl, alkyl of 1–6 carbons, ethyl, 1-propyl, 3-methyl-1-butyl and aminophenyl.

23. The method of claim 21, wherein the solid support matrix is selected from the group consisting of cellulose, nitrocellulose, cellulose acetate, polyacrylamide, agarose polyacrylamide copolymer, agarose, starch, nylon, nylon polyesters, dextran, cross-linked dextran, dextran acrylamide copolymer, cross-linked hydroxyethylmethacrylate, substituted cross-linked polystyrenes, polyvinylalcohol, wool, metal oxides, porous ceramics coated with hydrophilic organic polymers and glass.

24. The method of claim 21, wherein said solid support matrix is carboxy cellulose.

25. The method of claim 21, wherein said first pH is achieved with a buffer selected from the group consisting of MES, MOPS and HEPES.

26. The method of claim 21, wherein said second pH is achieved with a buffer selected from the group consisting of ammonium acetate or taurine.

27. The method of claim 21, wherein the sample comprises blood, plasma or serum.

* * * * *

UNITED STATES PATENT AND TRADEMARK OFFICE
CERTIFICATE OF CORRECTION

| | | |
|---|---|---|
| PATENT NO. | : 7,195,923 B2 | |
| APPLICATION NO. | : 10/061438 | |
| DATED | : March 27, 2007 | |
| INVENTOR(S) | : McCroskey et al. | |

It is certified that error appears in the above-identified patent and that said Letters Patent is hereby corrected as shown below:

Page 2, line 36, please delete "Glycernia" and insert therefore, --Glycemia--.

Page 2, Abstract item [57] line 14, please delete "usefi.il" and insert therefore, --useful--.

Column 8, lines 57-58, please delete "m-aminophenyboronic" and insert therefore, --m-aminophenylboronic--.

Column 10, line 58, please delete "("C")" and insert therefore, --("c")--.

Column 12, line 29, please delete "$Mg_{++}$" and insert therefore, --$Mg^{++}$--.

Column 12, line 50, please delete "hemoglbin" and insert therefore, --hemoglobin--.

Column 13, line 15, please delete "showed," and insert therefore, --showed--.

Column 13, lines 63-65, please delete "(Fig. 6C), the movement..................the surface)." and insert the same line on line 62.

Column 14, line 26, please delete "6D" and insert therefore, --6B--.

Column 14, line 63, please delete "$S_{y,x}$" and insert therefore, -- $S_{y.x}$--.

Column 15, line 14, please delete ""X"" and insert therefore, --"x"--.

Column 16, line 50, please delete "list" and insert therefore, --lists--.

Column 17, line 10, please delete "to" and insert therefore, --of--.

Column 20, line 13, please delete "and nonglycated" in Claim 21 before "hemoglobin".

Column 20, line 23, please delete "homoglobin" and insert therefore, --hemoglobin--.

Signed and Sealed this
First Day of November, 2011

David J. Kappos
*Director of the United States Patent and Trademark Office*